United States Patent
Racz

[11] Patent Number: 5,899,891
[45] Date of Patent: * May 4, 1999

[54] CATHETER

[75] Inventor: N. Sandor Racz, Greenfield Center, N.Y.

[73] Assignee: Epimed International, Inc., Gloversville, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/706,608

[22] Filed: Sep. 5, 1996

[51] Int. Cl.$^6$ .............................. A61M 25/00; A61M 5/00
[52] U.S. Cl. ........................... 604/280; 604/282; 604/264
[58] Field of Search ................................. 604/164, 165, 604/167, 170, 236, 256, 264, 270, 272, 273, 280, 282

[56] References Cited

U.S. PATENT DOCUMENTS

| | | | |
|---|---|---|---|
| 3,856,009 | 12/1974 | Winnie . | |
| 4,194,513 | 3/1980 | Rhine et al. | 128/750 |
| 4,518,383 | 5/1985 | Evans | 604/51 |
| 4,596,553 | 6/1986 | Lee | 604/49 |
| 4,610,671 | 9/1986 | Luther | 604/168 |
| 4,650,472 | 3/1987 | Bates | 604/158 |
| 4,721,117 | 1/1988 | Mar et al. | 604/170 |
| 4,863,424 | 9/1989 | Blake, III et al. | 604/54 |
| 4,955,862 | 9/1990 | Sepetka | 604/282 |
| 5,084,022 | 1/1992 | Claude | 604/164 |
| 5,106,369 | 4/1992 | Christmas | 604/51 |
| 5,106,376 | 4/1992 | Mononen et al. | 604/164 |
| 5,114,401 | 5/1992 | Stuart et al. | 604/53 |
| 5,129,889 | 7/1992 | Hahn et al. | 604/265 |
| 5,176,661 | 1/1993 | Evard et al | 604/282 |
| 5,178,158 | 1/1993 | de Toledo | 604/282 |
| 5,190,520 | 3/1993 | Fenton, Jr. et al. | 604/282 |
| 5,213,578 | 5/1993 | Heiliger et al. | 604/158 |
| 5,232,442 | 8/1993 | Johnson et al. | 604/51 |
| 5,263,947 | 11/1993 | Kay | 604/331 |
| 5,290,230 | 3/1994 | Ainsworth et al. | 604/282 |
| 5,308,342 | 5/1994 | Sepetka et al. | 604/282 |
| 5,348,541 | 9/1994 | Lyell | 604/164 |
| 5,356,388 | 10/1994 | Sepetka et al. | 604/256 |
| 5,382,238 | 1/1995 | Abrahamson et al. | 604/170 |
| 5,490,845 | 2/1996 | Racz | 604/266 |
| 5,514,236 | 5/1996 | Avellanet et al. | 604/167 |
| 5,531,690 | 7/1996 | Solar | 604/282 |
| 5,545,138 | 8/1996 | Fugoso et al | 604/282 |
| 5,746,692 | 5/1998 | Bacich et al. . | |

*Primary Examiner*—Wynn Wood Coggins
*Assistant Examiner*—Michael J. Hayes
*Attorney, Agent, or Firm*—Trask, Britt & Rossa

[57] ABSTRACT

Catheters which utilize a flexible tube that has been modified at one end or both ends. Such modifications involve modifying a tube end to increase rigidity and strength (while maintaining some flexibility), or involve special placement of an intraluminal cord within the tube. One such catheter has a tube (20) with a cord (26) running therethrough wherein a portion of the tube's proximal end has been reinforced (30), preferably, in such a manner that the reinforced portion of the tube remains flexible. Similarly, another catheter includes a tube having an associated intraluminal cord, wherein the cord is affixed to the interior of the tube's proximal end. Another catheter has a tube and intraluminal cord with an enlarged end (e.g. a ball (28)) extending from the tube's distal end, and is modified by incorporating, within the tube's distal end, a spring (30). The thus placed spring (30) acts to increase the rigidity of the tip of the device, and interacts with the ball if need be to collect a portion of the tube which may break off from the remainder of the tube after placement.

10 Claims, 3 Drawing Sheets

CATHETER

TECHNICAL FIELD

This invention generally relates to catheters for introducing fluids into body cavities. More specifically, the invention relates to small diameter catheters, such as epidural catheters, for introducing liquid medications into the spinal canal, spinal space, epidural space, blood vessels, and the like.

BACKGROUND

Among other things, U.S. Pat. 5,490,845 to Racz (Feb. 13, 1996) discloses a flexible catheter which includes a catheter tube containing an intraluminal cord member (cord) extending along the tube's length and protruding out of the tube's distal and proximal ends. The thus placed cord helps to prevent collapse of the tube during fluid administration, and the portion of the cord extending out of the tube's distal end also aids in the retention and removal of parts of the tube which might break off during use of the catheter.

DISCLOSURE OF THE INVENTION

Although fine for most applications, it has been found that by modifying the previously identified Racz catheter, even better performance can be achieved.

The invention includes catheters which utilize a flexible tube that has been modified at either one end or both ends. Such modifications generally involve strengthening the interior of a tube end by increasing its break strength and possibly its rigidity, but do not generally involve decreasing the tip's flexibility. In one embodiment, the tube end modifications involve special placement of an intraluminal cord contained within the tube.

In one aspect, the invention includes catheters which have been modified on the tube's proximal end. Thus, the invention includes a catheter having a tube with a cord running therethrough wherein a portion of the tube's proximal end has been reinforced, optionally, in such a manner that the reinforced portion of the tube remains flexible. Similarly, another catheter according to the invention includes a tube having an associated intraluminal cord, wherein the cord is affixed to the interior of the tube's proximal end, preferably at a strengthened portion. The distal end of the tube may be similarly modified.

In another aspect, a catheter of the type having a tube and intraluminal cord with an enlarged end (e.g. a ball or spherical member) extending from the tube's distal end, is modified by incorporating, within the tube's distal end, a support structure such as a coiled member having an interior diameter smaller than the cross-sectional diameter of the cord's enlarged portion. The thus placed coiled member acts both to increase the rigidity of the device (while maintaining flexibility), and still interact with the ball if need be to collect a portion of the tube which may break off the remainder of the tube.

BRIEF DESCRIPTION OF THE FIGURES

In the drawings, which depict presently preferred embodiments of the invention and in which like reference numerals refer to like parts in different views.

BEST MODE OF THE INVENTION

Figure 1:
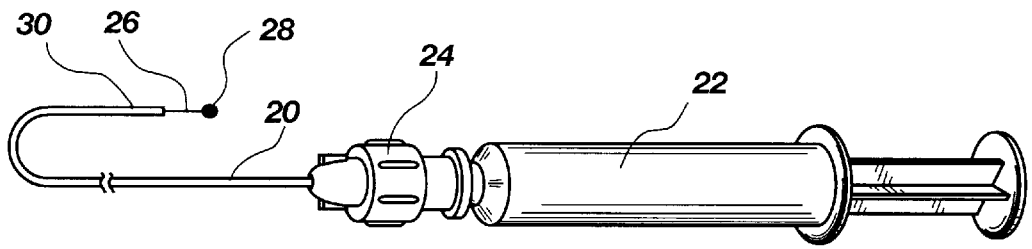
FIG. 1 depicts an embodiment of the present invention associated with a syringe.
Figure 2:
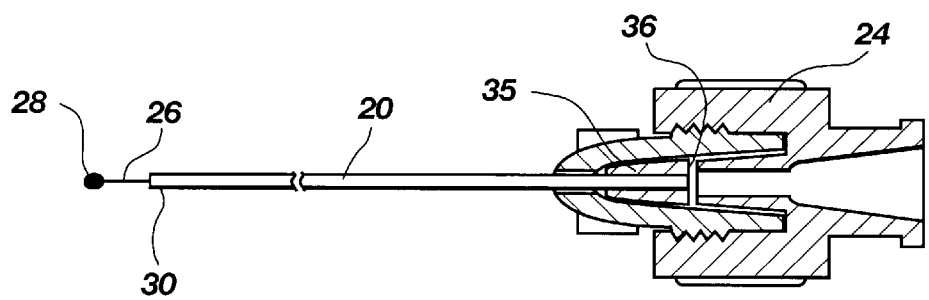
FIG. 2 depicts the embodiment of the preceding figure with a portion of a connector hub shown in cross-section.

As shown in FIGS. 1 and 2, a catheter tube 20 of the present invention is shown in conjunction with a syringe 22 having a connector hub 24 thereon. As shown, the catheter includes a hollow cylindrical member (tube) 20 having an intraluminal member ("inner line" or "cord") 26 extending therethrough terminating at enlarged end 28 thereof. Generally, the tube 20 will have a length from about twenty-five (25) centimeters (10 inches) to about ninety (90) centimeters (thirty-six inches). As shown in FIGS. 1 and 2, the end of the cord may extend from the lumen, and be free to move within the tube's lumen, however, the cord may alternatively be molded completely into the tubing (not shown), or glued on both ends to the tube's interior.

A preferred cord for use with catheters such as those disclosed herein includes a cable having several wound metal wires (made of, for example, stainless steel). The cord can also be a braided line including at least three optionally braided cables. Such cords are strong, hypoallergenic, and flexible. Alternatively, the cord may be made of a metal wire, other electrically conductive material, plastic (e.g. nylon), other polymers, silk, or other suitable material. The cord may be manufactured to contain anti-thrombogenic agents or other materials, so as to prevent, for example, occlusion of the catheter during longer term use. Other chemical agents which might be introduced include antiseptics and anesthetics.

Figure 3:
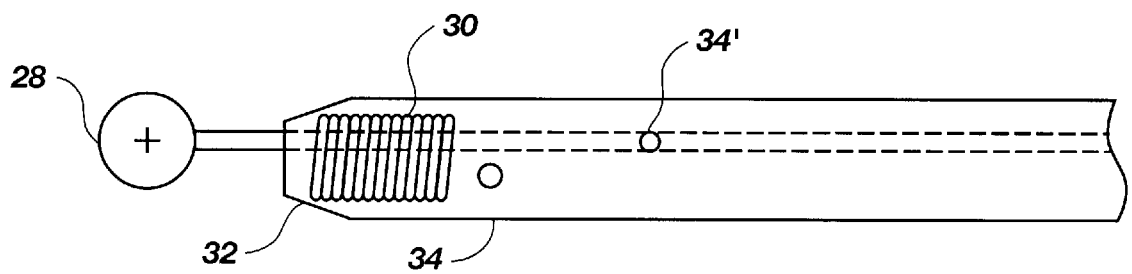
FIG. 3 depicts an enlarged, broken away view of the distal tube end of the embodiment of the preceding two figures.

The distal end of the catheter tube 20 of FIGS. 1 and 2 has been reinforced with a spring 30. The exterior cross-sectional diameter of the spring 30 approximates that of the cross-sectional diameter of the catheter's lumen (FIG. 3). The spring 30 may be glued, heat formed or melted to the tube 20. As shown in FIG. 3, the distal end of the tube may be formed as a tapered tip 32. As also shown in FIG. 3, the catheter tube 20 includes a plurality of apertures or holes 34 therein in the distal end so that should the enlarged end 28 block the lumen of the catheter tube 20, fluid may still pass through the holes 34.

Referring back to FIG. 2, the connector hub 24 is shown in conjunction with the catheter tube 20. The catheter tube 20 is retained within connector hub 24 by interaction of bushing 35 with the proximal end 36 of the catheter tube 20. In the event the cord 26 is not somehow affixed to the tube's proximal end, the cord may be trapped between the bushing 35 and the male portion of the connector hub 24.

Figure 4:
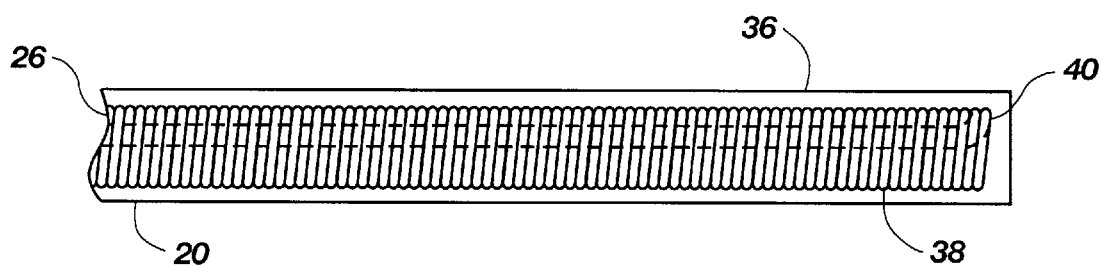
FIG. 4 depicts an enlarged, broken away view of the proximal tube end of the embodiment of the preceding three figures.

As depicted in FIG. 4, the inner line 26 is preferably associated (e.g. by adhesion, welding, molding or the like) to a coiled member 38 at weld 40, which coiled member (spring) is contained within the proximal end 36 of the tube 20. Adhesive is preferably placed along the length of the spring or around the circumference at the same as the weld 40. The coiled member 38 defines a lumen through which fluid flows (and thus also through the lumen of the tube 20) while still increasing the strength of the proximal end 36 of the tube.

Figure 5:
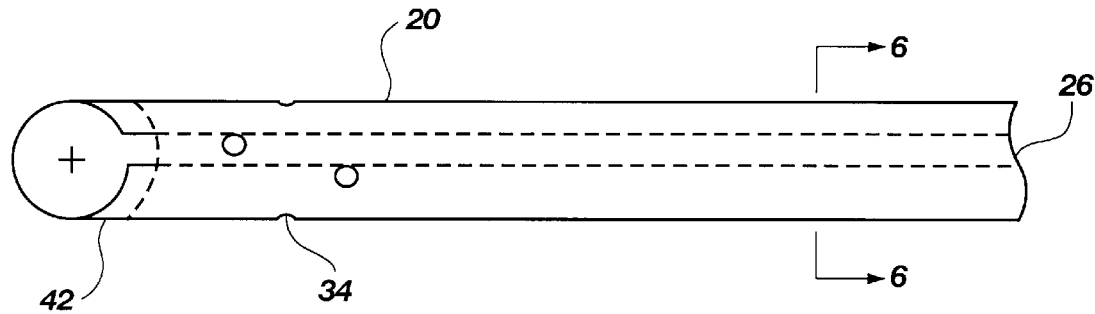
FIG. 5 depicts an enlarged, broken away view of an alternative embodiment of the distal end of a catheter tube according to the invention.
Figure 6:
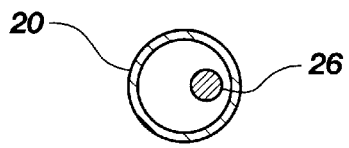
FIG. 6 is an enlarged, stylized, cross-sectional view of the distal end of the preceding figure taken along section line 6—6 of the preceding figure.

FIGS. 5 and 6 depict an alternative embodiment of a distal end of a catheter according to the invention. In that embodiment, the catheter tube 20 and inner line 26 are melted together to form a solid closed distal end 42. The length of the thus formed solid portion 42 is chosen (e.g. from about one-half to about twice the outer diameter of the tube) so as not to interfere with the holes 34, 34' while still increasing the strength of the distal end. Multiple eye holes (e.g. ones about 0.4 millimeters ("mm") (or about 0.015 inches) in diameter) are formed in the distal end of the catheter so as to allow the fluid to be transported by the catheter to pass therethrough.

Figure 7:
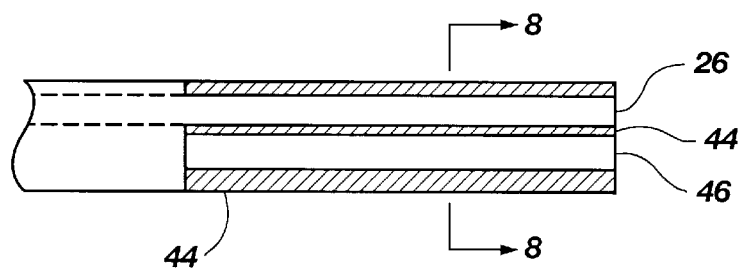
FIG. 7 depicts an enlarged, broken away view of an alternative embodiment of the proximal end of a catheter tube according to the invention.
Figure 8:
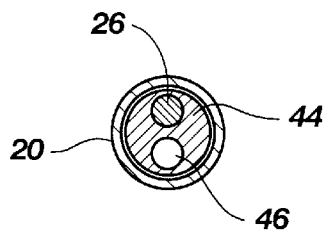
FIG. 8 is an enlarged, stylized, cross-sectional view of the embodiment of the preceding figure taken along section line 8—8 of the preceding figure.

FIGS. 7 and 8 depict an alternative embodiment of a proximal end of a catheter according to the invention. In that embodiment, the proximal end of the tube is modified and strengthened by incorporation of an adhesive 44 in the first one (1) to about four (4) centimeters of the tube. As shown in FIGS. 7 and 8, the adhesive is formed to contain a channel 46 (e.g. one having a diameter of about 0.3 mm (0.012 inches)) to allow fluid flow therethrough.

Figure 9:
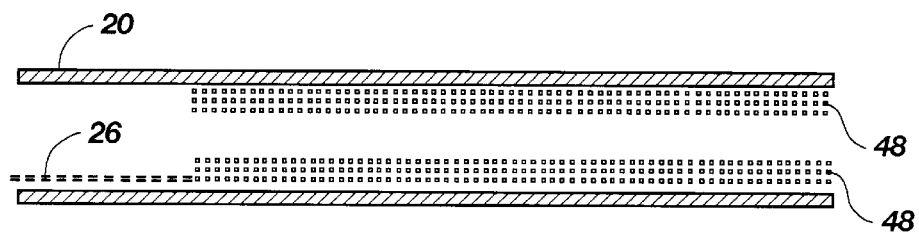
FIG. 9 depicts an enlarged, broken away view of an alternative embodiment of the proximal end of a catheter tube according to the invention.

FIG. 9 depicts an alternative embodiment of the invention wherein the, for example, proximal end of the tube 20 is modified by incorporating another piece of conduit 48 within the tube 20. The conduit piece preferably has an exterior diameter approximating that of the tube's cross-sectional diameter at the proximal end. The conduit piece can be made of the same or different material as the tube. Preferably, the conduit piece is more rigid than the tube. The cord 26 may be "sandwiched" between the conduit piece 48 and tube 20 or otherwise adhered to the proximal end 36.

Such a conduit piece can be used in conjunction with the previously described coiled member or spring on either one tube end or both of them.

Figure 10:
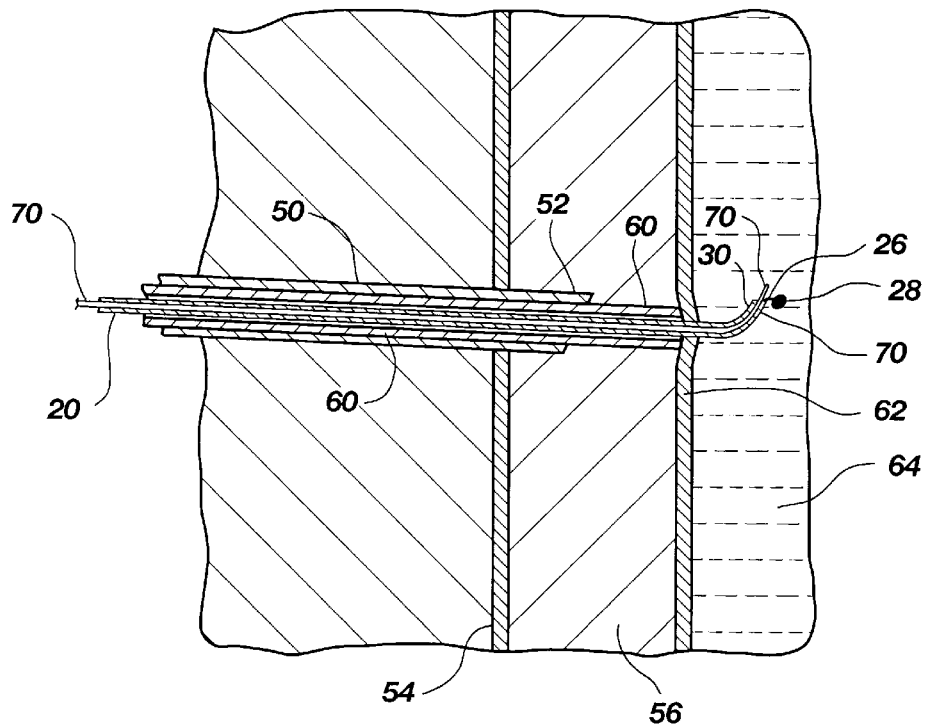
FIG. 10 is a cross-sectional view of an anesthesia assembly for use with the present invention.
Figure 11:
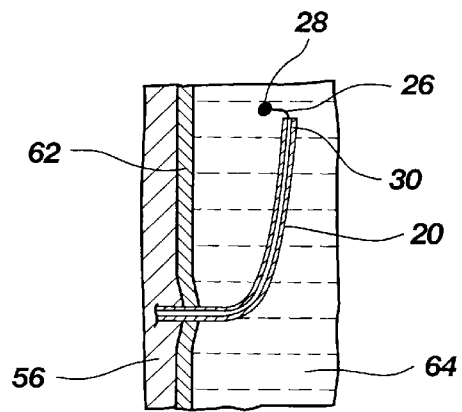
FIG. 11 is a cross-sectional view of an anesthesia assembly and a portion of the present invention in use.

Referring to FIGS. 10 and 11, a catheter tube 20 is shown in use in the spinal canal of a subject (e.g. a mammal, such as a human). An epidural needle 50 is inserted at a slight angle to a patient's skin until point 52 passes through ligament 54 and into the epidural space 56. Once the epidural space 56 has been reached by point 52 of needle 50, an introducer 60 is inserted through the lumen of needle 50 until it abuts dura wall 62. Subsequently the catheter tube 20 with stylet 70 in place is inserted through the lumen of the introducer 60. The stylet 70 penetrates the dura wall 62 by spreading the fibers thereof. Both the catheter tube 20 and stylet 70 are advanced into the subarachnoid space 64. Stylet 70 is then removed, and a syringe is used to withdraw spinal fluid to confirm the location of the end of catheter tube 20. The proximal end of the catheter tube 20 is maintained outside the patient's body and may be coupled to any desired tubing, syringe, etc. As can be readily seen, if any portion of the catheter tube 20 in the patient is broken, it can be retrieved by pulling on the integrated or non-integrated cord 26. Also if the catheter tube 20 should become kinked, the cord 26 will allow the flow of fluids through the catheter.

Although shown in use as an epidural catheter, the invention may also be used for intrathecal administration of medicines to a subject.

After being apprised of the devices according to the invention, methods of making them will become readily apparent to those of skill in the art. For instance, a catheter tube may be made of flexible pre-tapered, pre-holed TECHOTHANE 55D polyurethane tubing 0.9 mm (0.035 inch) outer diameter, 0.6 mm (0.025 inch) inner diameter) or nylon (e.g. PEBAX 55D). Alternatively, it can be made of a synthetic absorbable polymer in a manner similar to that disclosed in U.S. Pat. 5,129,889 to Hahn et al. (Jul. 14, 1992). The inner line may be, for example, twisted 0.009 1×2 stainless or 0.25 mm (0.010 inch) diameter nylon. The enlarged portion can thus have a diameter of 0.86 mm (0.035 inches). The coiled members may be made of 304 stainless spring (0.6 mm (0.024 inch) outer diameter, 0.4 mm (0.016 inch) inner diameter). The adhesive may be UV cured flexible adhesive (type AAS 2465 LV).

Furthermore, the catheter might otherwise be modified. For instance, the tube may be impregnated with barium to allow fluoro-imaging.

Although the invention has been described with regard to certain preferred embodiments, the scope of the invention is to be defined by the appended claims.

What is claimed is:

1. A catheter having a single lumen comprising:

a tube being flexible, said tube having an interior, a proximal end, and a distal end, the tube's proximal end conformed for association with a fluid delivery or receiving device, the tube's distal end adapted for insertion into a body cavity, and the tube's interior fluidically communicating the proximal and distal ends of the tube;

a cord having first and second ends, said cord running from said tube's proximal end, extending along said tube's interior, and extending to said tube's distal end;

a flexible spring placed within the proximal end of said tube whereby to increase said tube end's strength, said spring adhered to and completely contained within a portion of the proximal end of the tube, wherein the first end of the cord is adhered to said spring.

2. The catheter of claim 1 further comprising a second means for increasing a tube end's strength associated with the tube's distal end.

3. The catheter of claim 1 wherein said cord consists of several wound wires to form a cable.

4. A catheter having a single lumen comprising:

a tube being flexible, said tube having an interior, a proximal end, and a distal end, the tube's proximal end conformed for association with a fluid delivery or receiving device, the tube's distal end adapted for insertion into a body cavity, and the tube's interior fluidically communicating the proximal and distal ends of the tube;

a cord having first and second ends, said cord running from said tube's proximal end, extending along said tube's interior, and extending to said tube's distal end; and flexible means for increasing a tube end's strength, said flexible means adhered and completely contained within a portion of the tube's proximal end; and wherein the flexible means for increasing a tube end's strength is adhesive placed interior the first centimeter to about the first four centimeters of the tube, said adhesive formed to contain a channel defining a portion of said single lumen whereby to allow fluid to flow therethrough.

5. The catheter of claim 4 wherein one end of said cord is adhered to the means for increasing a tube end's strength.

6. The catheter of claim 4 further comprising a second means for increasing a tube end's strength associated with the tube's distal end.

7. A single lumen catheter comprising:
 (a) a tube being flexible, said tube having an interior, a proximal end, and a distal end, the tube's proximal end conformed for association with a fluid delivery or receiving device, the tube's distal end adapted for insertion into a body cavity, and the tube's interior forming the single lumen within the catheter, and fluidically communicating the proximal and distal ends of said tube; and
 (b) a cord having first and second ends, said cord running from said tube's proximal end, extending along said tube's interior, and extending to said tube's distal end, the cord's first end being fixedly adhered to the interior of said tube's proximal end, the remainder of the cord being capable of free lateral movement within the interior of said tube.

8. The catheter of claim 7 wherein said cord comprises several wound wires forming a cable.

9. The catheter of claim 8 wherein the cable is braided.

10. A catheter comprising:
 a tube being flexible, said tube having an interior, a proximal end, and a distal end, the tube's proximal end conformed for association with a fluid delivery or receiving device, the tube's distal end adapted for insertion into a body cavity, and the tube's interior fluidically communicating the proximal and distal ends of said tube; and
 a cord having first and second ends, said cord running from said tube's proximal end, extending along said tube's interior, and extending to said tube's distal end, the cord's first end being fixedly adhered to the interior of said tube's proximal end, the remainder of the cord being capable of free lateral movement within the interior of said tube; and
 a coiled member contained within the proximal end of said tube and extending inwardly therefrom, towards the distal end, said cord's proximal end fixedly attached to said coiled member.

* * * * *